United States Patent [19]

Cotterrell

[11] 4,048,172
[45] Sept. 13, 1977

[54] CARBONYLMETHYLPYRIMIDIN-6-YL PHOSPHATES AND PHOSPHOROTHIONATES

[75] Inventor: Graham Paul Cotterrell, Wokingham, England

[73] Assignee: Imperial Chemical Industries Limited, London, England

[21] Appl. No.: 598,879

[22] Filed: July 24, 1975

Related U.S. Application Data

[62] Division of Ser. No. 451,368, March 14, 1974, Pat. No. 3,932,631.

[30] Foreign Application Priority Data

Mar. 29, 1973 United Kingdom ............. 15159/73

[51] Int. Cl.$^2$ ............................................. C07F 9/65
[52] U.S. Cl. ........................ 260/256.5 R; 260/251 P
[58] Field of Search ...................... 260/256.5 R, 251 P

[56] References Cited

U.S. PATENT DOCUMENTS

| | | | |
|---|---|---|---|
| 3,287,453 | 1/1966 | McHattie | 260/256.5 R |
| 3,651,224 | 3/1972 | Sharpe et al. | 424/200 |
| 3,657,247 | 4/1972 | Freeman et al. | 424/200 X |
| 3,808,333 | 4/1974 | Milzner | 260/256.5 R |
| 3,932,631 | 1/1976 | Cotterrell | 424/200 |

Primary Examiner—Leonard Schenkman
Attorney, Agent, or Firm—Cushman, Darby & Cushman

[57] ABSTRACT

Pesticidally active compounds of the formula

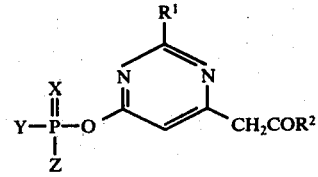

wherein X is oxygen or sulphur; Y is alkoxy containing from one to four carbon atoms, alkylamino containing from one to four carbon atoms, or dialkylamino containing from one to four carbon atoms in each alkyl moiety; Z is alkoxy containing from one to four carbon atoms; $R^1$ is alkyl containing from one to four carbon atoms, phenyl, chlorophenyl, alkylamino containing from one to four carbon atoms, dialkylamino containing from one to four carbon atoms in each alkyl moiety, or N-carboxylic acyl alkylamino containing from one to four carbon atoms in the carboxylic acyl moiety and from one to four carbon atoms in the alkyl moiety; and $R^2$ is alkoxy containing from one to four carbon atoms, amino, alkylamino containing from one to four carbon atoms, dialkylamino containing from one to four carbon atoms in each alkyl moiety, or alkenyl amino containing three to five carbon atoms.

4 Claims, No Drawings

CARBONYLMETHYLPYRIMIDIN-6-YL PHOSPHATES AND PHOSPHOROTHIONATES

This is a division of application Ser. No. 451,368, filed Mar. 14, 1974, now U.S. Pat. No. 3,932,631.

This invention relates to novel organophosphorus compounds, processes for preparing them, compositions comprising them and methods of combating pests using them.

Accordingly the present invention provides compounds of formula:

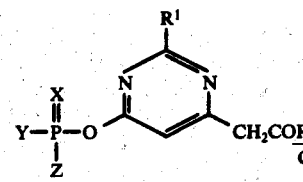

wherein X is oxygen or sulphur; Y is alkoxy containing from one to four carbon atoms, alkylamino containing from one to four carbon atoms, or dialkylamino containing from one to four carbon atoms in each alkyl moiety; Z is alkoxy containing from one to four carbon atoms; $R^1$ is alkyl containing from one to four carbon atoms, phenyl which may optionally be substituted with halogen, alkylamino containing from one to four carbon atoms, dialkylamino containing from one to four carbon atoms in each alkyl moiety, or N-carboxylic acyl alkylamino containing from one to four carbon atoms in the carboxylic acyl moiety and from one to four carbon atoms in the alkyl moiety; and $R^2$ is alkoxy containing from one to four carbon atoms, amino, alkylamino containing from one to four carbon atoms, dialkylamino containing from one to four carbon atoms in each alkyl moiety, or alkenyl amino containing from three to five carbon atoms.

Preferred compounds according to the present invention are those wherein X is oxygen or sulphur; Y and Z are alkoxy containing from one to four carbon atoms; $R^1$ is alkyl containing from one to four carbon atoms or dialkylamino containing from one to four carbon atoms in each alkyl moiety; and $R^2$ is alkoxy containing from one to four carbon atoms.

Specific compounds according to the invention include those set out in Table 1 below. All the compounds conform to the formula:

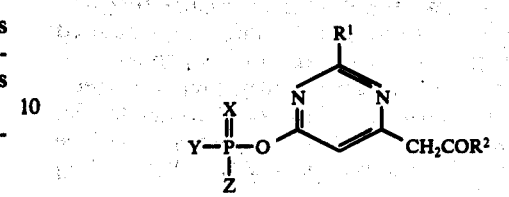

and the meanings of X, Y, Z, $R^1$ and $R^2$ are set out in the Table, together with a physical characteristic, for each compound.

TABLE I

| Compound No | X | Y | Z | $R^1$ | $R^2$ | Physical Characteristic |
|---|---|---|---|---|---|---|
| 1 | S | $OCH_3$ | $OCH_3$ | $CH_3$ | $OC_2H_5$ | viscous oil |
| 2 | S | $OC_2H_5$ | $OC_2H_5$ | $CH_3$ | $OC_2H_5$ | $n_D^{14}$ 1.4950 |
| 3 | S | $OC_2H_5$ | $OC_2H_5$ | $4\text{-Cl}-C_6H_5$ | $OC_2H_5$ | m.p. 63° C |
| 4 | S | $OC_2H_5$ | $OC_2H_5$ | $CH(CH_3)_2$ | $OC_2H_5$ | viscous oil |
| 5 | S | $OC_2H_5$ | $OC_2H_5$ | $N(C_2H_5)_2$ | $OCH_3$ | $n_D^{23}$ 1.5165 |
| 6 | S | $OCH_3$ | $OCH_3$ | $N(C_2H_5)_2$ | $OC_2H_5$ | $n_D^{20}$ 1.5225 |
| 7 | O | $OC_2H_5$ | $OC_2H_5$ | $N(C_2H_5)_2$ | $OC_2H_5$ | $n_D^{25}$ 1.4952 |
| 8 | S | $OC_2H_5$ | $OC_2H_5$ | $NHC_2H_5$ | $OC_2H_5$ | $n_D^{24}$ 1.5170 |
| 9 | S | $OCH_3$ | $OCH_3$ | $NHC_2H_5$ | $OC_2H_5$ | $n_D^{24}$ 1.5290 |
| 10 | O | $N(CH_3)_2$ | $OC_2H_5$ | $N(C_2H_5)_2$ | $OC_2H_5$ | $n_D^{21.5}$ 1.4878 |
| 11 | S | $OC_2H_5$ | $OC_2H_5$ | $N(C_2H_5)_2$ | $OC_2H_5$ | $n_D^{22.5}$ 1.5097 |
| 12 | O | $NHCH_3$ | $OCH_3$ | $N(C_2H_5)_2$ | $OC_2H_5$ | viscous oil |
| 13 | S | $OCH_3$ | $OCH_3$ | $NC_2H_5$ / $COCH_3$ | $OC_2H_5$ | $n_D^{27.5}$ 1.5180 |
| 14 | S | $OC_2H_5$ | $OC_2H_5$ | $NC_2H_5$ / $COCH_3$ | $OC_2H_5$ | viscous oil |
| 15 | S | $OC_2H_5$ | $OC_2H_5$ | $N(C_2H_5)_2$ | $NH_2$ | m.p. 76° C |
| 16 | S | $OC_2H_5$ | $OC_2H_5$ | $N(C_2H_5)_2$ | $NHCH_2CH=CH_2$ | $n_D^{17}$ 1.5317 |
| 17 | S | $OC_2H_5$ | $OC_2H_5$ | $N(C_2H_5)_2$ | $NHC_4H_9(n)$ | $n_D^{17}$ 1.5233 |
| 18 | S | $OC_2H_5$ | $OC_2H_5$ | $NHC_2H_5$ | $NHC_4H_9(n)$ | m.p. 70° C |
| 19 | O | $N(CH_3)_2$ | $OC_2H_5$ | $N(C_2H_5)_2$ | $NHC_2H_5$ | $n_D^{17}$ 1.5135 |
| 20 | O | $OCH_3$ | $OCH_3$ | $N(C_2H_5)_2$ | $NHC_2H_5$ | m.p. 76° C |

All the compounds listed hereinabove in Table I were identified as possessing the structural formulae assigned to them by nuclear magnetic resonance and infra-red spectroscopy, and gave satisfactory elemental microanalysis.

The invention compounds may be prepared by treating a hydroxy pyrimidine of formula:

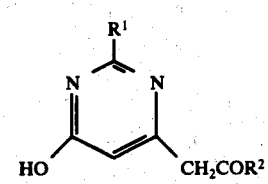

or an alkali metal salt thereof, with a compound of formula:

wherein Q is halogen and X, Y, Z, $R^1$ and $R^2$ have any of the meanings given hereinabove. The treatment is preferably carried out in a solvent or diluent, and optionally in the presence of a base. Q is preferably chlorine or bromine, and when an alkali metal salt of the hydroxy pyrimidine is used it is preferably the sodium salt. When carried out in the presence of a base a preferred base is an alkali metal carbonate, for example potassium carbonate. Suitable solvents include esters such as ethyl acetate and ketones such as acetone, methyl isobutyl ketone or cyclohexanone. When an alkali metal salt of the hydroxy pyrimidine is employed it may be suspended in a diluent such as, for example, toluene. The reactions may be carried out at temperatures within the range of 0° C to 150° C, and preferably within the range 15° C to 100° C. The compounds of the invention are generally viscous liquids or low melting solids.

The hydroxy pyrimidines of formula:

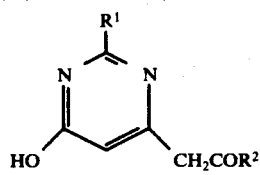

wherein $R^1$ and $R^2$ have any of the meanings given hereinabove, and which are utilised as intermediates in the preparation of the invention compounds, may be prepared by esterification or amidification of the corresponding pyrimidine acetic acid derivatives of formula:

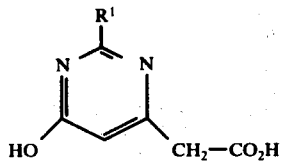

the preparation of which is described in our co-pending British Patent application No. 964/73. These esterification and amidification processes are carried out in the conventional manner, and examples of such processes are given hereinbelow to illustrate the preparation of the intermediates. Table 2 lists the specific hydroxy pyrimidine intermediates which have been used in the preparation of the invention compounds set out in Table 1. In Table 2 the values of $R^1$ and $R^2$ for each intermediate, together with its melting point are given.

TABLE 2

| Intermediate No | $R^1$ | $R^2$ | Melting point ° C |
| --- | --- | --- | --- |
| A | $CH_3$ | $OC_2H_5$ | 127 |
| B | $4\text{-Cl}-C_6H_5$ | $OC_2H_5$ | 170 |
| C | $CH(CH_3)_2$ | $OC_2H_5$ | 107 |
| D | $N(C_2H_5)_2$ | $OCH_3$ | 113 |
| E | $N(C_2H_5)_2$ | $OC_2H_5$ | 101 |
| F | $NHC_2H_5$ | $OC_2H_5$ | 109 |
| G | $NC_2H_5$<br>|<br>$COCH_3$ | $OC_2H_5$ | 75 |
| H | $N(C_2H_5)_2$ | $NH_2$ | 229 |
| I | $N(C_2H_5)_2$ | $NHCH_2CH=CH_2$ | 194 |
| J | $N(C_2H_5)_2$ | $NHC_4H_9(n)$ | 189 |
| K | $NHC_2H_5$ | $NHC_4H_9(n)$ | 191 |
| L | $N(C_2H_5)_2$ | $NHC_2H_5$ | 210 |

The invention compounds exhibit pesticidal, and particularly insecticidal, properties, and may be utilised to combat insect pests of plants, stored products, and the like. They may be particularly usefully employed in agriculture and horticulture when formulated into compositions with various agriculturally and horticulturally acceptable diluent or carrier materials.

In a further aspect therefore the present invention provides pesticidal compositions comprising as an active ingredient a compound of formula:

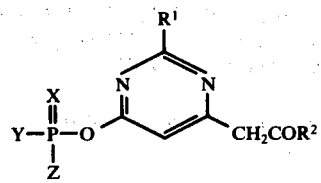

wherein X, Y, Z, $R^1$ and $R^2$ have any of the meanings as hereinbefore defined, together with a diluent.

The compositions may be in the form of dusting powders wherein the active ingredient is mixed with a solid diluent or carrier, for example, kaolin, bentonite, kieselguhr, or talc, or they may be in the form of granules, wherein the active ingredient is absorbed on a porous granular material, for example, pumice.

Alternatively the compositions may be in the form of liquid preparations to be used as dips or sprays, which are generally aqueous dispersions or emulsions of the active ingredients in the presence of one or more known wetting agents, dispersing agents or emulsifying agents. These compositions are prepared by dissolving the active ingredient in a suitable solvent, for example, a ketonic solvent such as diacetone alcohol, and adding the mixture so obtained to water which may contain one or more known wetting, dispersing or emulsifying agents.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water in order to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient or ingredients may be used.

The compositions of the present invention may, if desired, also comprise in addition to a compound of the present invention, at least one other biologically-active ingredient, for example an insecticide, or a fungicide.

In use the compositions are applied to the pests, to the locus of the pests, to the habitat of the pests, or to growing plants liable to infestation by the pests, by any of the known means of applying pesticidal compositions for example, by dusting or spraying.

The compounds of the invention and compositions comprising them are very toxic to wide varieties of insect and other invertebrate pests, including, for example, the following:

Tetranychus telarius (red spider mite)
Aphis fabae, (aphids)
Megoura viceae (aphids)
Aedes aegypti (mosquitos)

*Dysdercus fasciatus* (capsids)
*Musca domestica* (houseflies)
*Blatella germanica* (cockroaches)
*Pieris brassicae* (white butterfly, larvae)
*Plutella maculipennis* (diamond black moth, larvae)
*Phaedon cochleariae* (mustard beetle)
*Calandra granaria* (grain beetle)
*Tribolium confusum* (flour beetle)
*Cydia pomonella* (codling moth)
*Leptinotarsa decemlineata* (colorado beetle)
*Agriolimax reticulatus* (slugs)

The invention is illustrated by the following Examples.

EXAMPLE 1

This Example illustrates the preparation of 2-diethylamino-4-ethoxycarbonylmethyl-6-hydroxyprimidine (Intermediate E, Table 2), useful as an intermediate in the preparation of compounds of the invention.

Dry absolute ethanol (250 ml) was saturated with dry hydrogen chloride gas at 20° C and to the solution was added at 15° C 2-dimethylamino-6-hydroxy-pyrimidin-6-yl acetic acid (40.5 g) with stirring. The mixture was stirred for 16 hours at the ambient temperature (ca 22°–24° C) and the volatile fraction evaporated under reduced pressure to leave an oil which crystallised on standing. This was dissolved in water, and the solution neutralised with aqueous 2N sodium hydroxide solution. The precipitate which formed was collected by filtration, washed with water and recrystallised from aqueous ethanol to yield 2-diethylamino-4-ethoxy-carbonylmethyl-6-hydroxypyrimidine, m.p. 98°–100° C.

EXAMPLE 2

By procedures similar to that illustrated in Example 1, the following intermediate hydroxy pyrimidines were prepared as follows:

2-Methyl-4-ethoxycarbonylmethyl-6-hydroxypyrimidine (Intermediate A, Table 2) from 2-methyl-6-hydroxy-pyrimidin-4-yl acetic acid and ethanol;
2(4-chlorophenyl)-4-ethoxycarbonylmethyl-6-hydroxypyrimidine (Intermediate B, Table 2) from 2(4-chlorophenyl)-6-hydroxypyrimidin-4-yl acetic acid and ethanol;
2-isopropyl-4-ethoxycarbonylmethyl-6-hydroxypyrimidine (Intermediate C, Table 2) from 2-isopropyl-6-hydroxypyrimidin-4-yl acetic acid and ethanol;
2-diethylamino-4-methoxycarbonylmethyl-6-hydroxypyrimidine (Intermediate D, Table 2) from 2-diethylamino-6-hydroxypyrimidin-4-yl acetic acid and methanol; and
2-ethylamino-4-ethoxycarbonylmethyl-6-hydroxypyrimidine (Intermediate F, Table 2) from 2-ethylamino-6-hydroxypyrimidin-4yl acetic acid and ethanol.

2-N-Ethylacetamido-4-ethoxycarbonylmethyl-6-hydroxypyrimidine (Intermediate G, Table 2) was prepared as follows:

A mixture of 2-ethylamino-4-ethoxycarbonylmethyl-6-hydroxypyrimidine (Intermediate F, Table 2) and an excess of acetic anhydride was warmed to 80°–100° C for 15 minutes and then poured into iced water. The precipitate was collected by filtration, washed with water and recrystallised from ethanol to yield 2-N-ethylacetamido-4-ethoxycarbonylmethyl-6-hydroxypyrimidine.

EXAMPLE 3

This Example illustrates the preparation of 2-diethylamino-4-N-ethylcarbamoylmethyl-6-hydroxypyrimidine (Intermediate L, Table 2).

A mixture of 2-diethylamino-4-ethoxycarbonylmethyl-6-hydroxypyrimidine (Intermediate E, 15.0 g), industrial methylated spirit (20 ml) and aqueous ethylamine solution (70% w/v, 40 ml) was kept at the ambient temperature for 20 hours, after which the volatile portion was evaporated under reduced pressure. The residual solid was recrystallised from industrial methylated spirit to yield 2-diethylamino-4-N-ethylcarbamoylmethyl-6-hydroxypyrimidine, melting point 210° C.

EXAMPLE 4

By a procedure similar to that illustrated in Example 3 above, but utilizing the appropriate amine in place of aqueous ethylamine, the following compounds were also prepared:

2-Diethylamino-4-carbamoylmethyl-6-hydroxypyrimide (Intermediate H, Table 2) from Intermediate E and ammonia (s.g. 0.880);
2-diethylamino-4-N-allylcarbamoylmethyl-6-hydroxypyrimidine (Intermediate I, Table 2) from Intermediate E and allylamine;
2-diethylamino-4-N-n-butylcarbamoylmethyl-6-hydroxypyrimidine (Intermediate J, Table 2) from Intermediate E and n-butylamine; and
2-ethylamino-4-N-n-butylcarbamoylmethyl-6-hydroxypyrimidine (Intermediate K, Table 2) from 2-ethylamino-4-ethoxycarbonylmethyl-6-hydroxypyrimidine (Intermediate F) and n-butylamine.

EXAMPLE 5

This Example illustrates the preparation of O,O-dimethyl O-2-diethylamino-4-ethoxy-carbonylmethylpyrimidin-6-yl phosphorothionate (Compound No. 6 Table 1).

A mixture of anhydrous potassium carbonate (2.84 g) 2-diethylamino-4-ethoxycarbonylmethyl-6-hydroxypyrimidine (2.6 g), dimethylphosphorochloridothionate (1.8 g) in dry acetone (50 ml) was stirred at the ambient temperature for 24 hours, after which the solid was removed by filtration and the filtrate evaporated under reduced pressure. The residual oil was disolved in methylene chloride, and the solution washed with 2% w/v aqeuous sodium hydroxide solution (2×20 ml) and with brine (2×20 ml), dried over anhydrous sodium sulphate and evaporated to give a residual oil. This was purified by preparative thin-layer chromatography (Silicagel F254 eluent: acetone/hexane (1:5) to yield O,O-dimethyl O-2-diethylamino-4-ethoxycarbonylmethylpyrimidin-6-yl phosphorothionate as a pale yellow oil, $n_D^{20}$ 1.5225, which gave satisfactory elemental and n.m.r. analysis.

$C_{14}H_{24}N_3O_5SP$ requires: C, 44.85; H, 6.4; N, 11.1%; found: C, 44.7; H, 6.4; N, 11.3%.

EXAMPLE 6

This example illustrates the preparation of N-dimethyl-O-ethyl O-2-diethylamino-4-ethoxy-carbonylmethylpyrimidin-6-yl phosphoramidate (Compound No. 10, Table 1).

To a solution of sodium (0.364 g) in dry ethanol (30 ml) was added 2-diethylamino-4-ethoxycarbonylmethyl-6-hydroxypyrimidine (4.0 g) and the resultant solution was stirred for 60 minutes. The solvent was then removed by evaporation under reduced pressure, the final traces of solvent being removed by azeotropic distillation with dry toluene. The residual solid was powdered and suspended in dry toluene (40 ml) and N-dimethyl-O-ethylphosphorochloridate (2.7 g) added to the stirred suspension. Stirring was continued for 16 hours at the ambient temperature, followed by a period of 6 hours at 60° C. The mixture was then cooled to the ambient temperature, washed with a solution of sodium hydroxide in brine (2% w/v; 3 × 10 ml), and with brine (2 × 15 ml). The toluene solution was then dried over anhydrous magnesium sulphate, and the solvent evaporated under reduced pressure. Final traces of solvent were volatilised by warming the residual oil at 40° C at a pressure of 0.7 mm. Hg., to yield N-dimethyl-O-ethyl O-2-diethylamino-4-ethoxycarbonylmethylpyrimidin-6-yl phosphoramidate, $n_D^{21.5}$ 1.4878.

$C_{16}H_{29}N_4O_5P$ requires: C, 49.5; H, 7.5; N, 14.4%; found: C, 49.9; H, 7.5; N, 14.2%.

EXAMPLE 7

This example illustrates the preparation of O,O-dimethyl O-2-N-ethylacetamido-4-ethoxycarbonylmethylpyrimidin-6-yl phosphorothionate (Compound No. 13, Table 1).

A mixture of 2-N-ethylacetamido-4-ethoxycarbonylmethyl-6-hydroxypyrimidine (4.0 g), anhydrous potassium carbonate (4.33 g), O,O-dimethylphosphorochloridothionate (2.65 g) and dry acetone (50 ml) was stirred at the ambient temperature for 20 hours. The insoluble residue was separated by filtration and the filtrate evaporated under reduced pressure to yield a residual oil. This was dissolved in methylene chloride (80 ml) and washed with dilute aqueous sodium hydroxide solution (2% w/v; 2 × 15 ml) and with water (2 × 20 ml). After drying the methylene chloride solution over anhydrous sodium sulphate, the solvent was removed by evaporation under reduced pressure. The residual oil was freed from the last traces of solvent by warming to 35°-40° C at 0.5 mm Hg. to yield O,O-dimethyl O-2-N-ethylacetamido-4-ethoxycarbonylmethylpyrimidin-6-yl phosphorothionate, $n_D^{27.5}$ 1.5180.

$C_{14}H_{22}N_3O_6SP$ requires: C, 43.0; H, 5.6%; found: C, 43.0; H, 5.9%.

EXAMPLE 8

This example illustrates the preparation of O,O-dimethyl O-2-diethylamino-4-N-ethylcarbamoylmethylpyrimidin-6-yl phosphate (Compound No. 20, Table 1). A mixture of 2-diethylamino-5-N-ethylcarbamoylmethyl-6-hydroxypyrimidine (2.0 g), anhydrous potassium carbonate (2.2 g), dimethylphosphorochloridate (1.4 g) and dry acetone (60 ml) was stirred at the ambient temperature for 72 hours. After filtration to remove the insoluble residue the filtrate was added to methylene chloride (80 ml), washed with water (2 × 15 ml) and with brine (2 × 15 ml) and dried over anhydrous magnesium sulphate. The solvent was removed by evaporation under reduced pressure and the residual solid recrystallised from ether to yield O,O-dimethyl O-2-diethylamino-4-N-ethylcarbamoylmethylpyrimidin-6-yl phosphate, melting point 76° C.

$C_{14}H_{25}N_4O_5P$ requires: C, 46.55; H, 6.9; N, 15.5%; found: C, 46.8; H, 6.9; N, 15.6%.

EXAMPLE 9

This example illustrates the preparation of O,O-diethyl O-2-ethylamino-4-N-n-butylcarbamoylmethylpyrimidin-6-yl phosphorothionate (Compound No. 18 Table 1).

A mixture of 2-ethylamino-4-N-n-butylcarbamoylmethyl-6-hydroxypyrimidine (2.0 g), anhydrous potassium carbonate (2.2 g), diethylphosphorochloridothionate (1.6 g) and dry acetone (50 ml) was stirred at the ambient temperature for 48 hours. After removal of the insoluble residue by filtration the filtrate was evaporated under reduced pressure, and the residual solid recrystallised from a mixture of diethyl ether and petroleum ether (boiling range 40° to 60° C) to yield O,O-diethyl O-2-ethylamino-4-N-n-butylcarbamoylmethylpyrimidin-6-yl phosphorothionate, melting point 70° C.

$C_{18}H_{34}N_4O_4SP$ requires: C, 47.5; H, 7.2; N, 13.85%; found: C, 47.2; H, 7.4; N, 13.7%.

EXAMPLE 10

The procedure of Example 8 was used to prepare other compounds according to the invention from the appropriate intermediates as follows:

O,O-Dimethyl O-2-methyl-4-ethoxycarbonylmethylpyrimidin-6-yl phosphorothionate (Compound No. 1, Table 1) from 2-methyl-4-ethoxy-carbonylmethyl-6-hydroxypyrimidine and dimethyl-phosphorochloridothionate;

O,O-diethyl O-2-methyl-4-ethoxycarbonylmethylpyrimidin-6-yl phosphorothionate (Compound No. 2, Table 1) from 2-methyl-4-ethoxycarbonylmethyl-6-hydroxypyrimidine and diethylphosphorochloridothionate;

O,O-diethyl O-2(4-chlorophenyl)-4-ethoxycarbonylmethylpyrimidin-6-yl phosphorothionate (Compound No. 3, Table 1). from 2(4-chlorophenyl)-4-ethoxycarbonylmethyl-6-hydroxypyrimidine and diethylphosphorochloridothionate, O,O-diethyl O-2-isopropyl-4-ethoxycarbonylmethylpyrimidin-6-yl phosphorothionate (Compound No. 4, Table 1) from 2-isopropyl-4-ethoxycarbonylmethyl-6-hydroxypyrimidine and diethylphosphorochloridothionate;

O,O-diethyl O-2-diethylamino-4-methoxycarbonylmethylpyrimidin-6-yl phosphorothionate (Compound No. 5, Table 1) from 2-diethylamino-4-methoxycarbonylmethyl-6-hydroxypyrimidine and diethylphosphorochloridothionate;

O,O-diethyl O-2-diethylamino-4-ethoxycarbonylmethylpyrimidin-6-yl phosphate (Compound No. 7, Table 1) from 2-diethylamino-4-ethoxycarbonylmethyl-6-hydroxypyrimidine and diethylphosphorochloridate;

O,O-diethyl O-2-ethylamino-4-ethoxycarbonylmethylpyrimidin-6-yl phosphorothionate (Compound No. 8, Table 1) from 2-ethylamino-4-ethoxycarbonylmethyl-6-hydroxypyrimidine and diethylphosphorochloridothionate;

O,O-dimethyl O-2-ethylamino-4-ethoxycarbonylmethylpyrimidin-6-yl phosphorothionate (Compound No. 9, Table 1) from 2-ethylamino-4-ethoxycarbonylmethyl-6-hydroxypyrimidine and dimethylphosphorochloridothionate;

O,O-diethyl O-2-diethylamino-4-ethoxycarbonylmethyl-pyrimidin-6-yl phosphorothionate (Compound No. 11, Table 1) from 2-diethylamino-4-ethoxycarbonylmethyl-6-hydroxypyrimidine and diethylphosphorochloridothionate;

N-methyl-O-methyl O-2-diethylamino-4-ethoxycarbonylmethylpyrimidin-6-yl phosphoramidate (Compound No. 12, Table 1) from 2-diethylamino-4-ethoxycarbonylmethyl-6-hydroxypyrimidine and N-methyl-O-methylphosphoramidochloridate;

O,O-diethyl O-2-N-ethylacetamido-4-ethoxycarbonylmethylpyrimidin-6-yl phosphorothionate (Compound No. 14 Table 1), from 2-N-ethylacetamido-4-ethoxycarbonylmethyl-6-hydroxypyrimidine and diethylphosphorochloridothionate;

O,O-diethyl O-2-diethylamino-4-carbamoylmethylpyrimidin-6-yl phosphorothionate (Compound No. 15, Table 1) from 2-diethylamino-4-carbamoylmethyl-6-hydroxypyrimidine and diethylphosphorochloridothionate;

O,O-diethyl O-2-diethylamino-4-N-allylcarbamoylmethylpyrimidin-6-yl phosphorothionate (Compound No. 16, Table 1) from 2-diethylamino-4-N-allylcarbamoylmethyl-6-hydroxypyrimidine and diethylphosphorochloridothionate;

O,O-diethyl O-2-diethylamino-4-N-n-butylcarbamoylmethyl pyrimidin-6-yl phosphorothionate (Compound No. 17, Table 1) from 2-diethylamino-4-N-n-butylcarbamoylmethyl-6-hydroxypyrimidine and diethylphosphorochloridothionate; and N-dimethyl-O-ethyl O-2-diethylamino-4-N-ethylcarbamoylmethylpyrimidin-6-yl phosphoramidate (Compound No. 19, Table 1) from 2-diethylamino-4-N-ethylcarbamoyl-methyl-6-hydroxypyrimidine and N-dimethyl-O-ethyl-phosphoramidochloridate.

EXAMPLE 11

5 parts by weight of O,O-dimethyl O-2-diethylamino-4-ethoxycarbonylmethylpyrimidin-6-yl phosphorothionate (Compound No. 6, Table 1) were thoroughly mixed in a suitable mixer with 95 parts by weight of talc. There was thus obtained a dusting powder.

EXAMPLE 12

10 parts by weight of O,O-diethyl-O-2-isopropyl-4-ethoxycarbonylmethylpyrimidin-6-yl phosphorothionate (Compound No. 4, Table 1), 10 parts of an ethylene oxide-octylphenol condensate ("Lissapol" NX; "Lissapol" is a Trade Mark) and 80 parts by weight of diacetone alcohol were thoroughly mixed. There was thus obtained a concentrate which, in mixing with water, gave an aqueous dispersion suitable for application as a spray in the control of insect pests.

EXAMPLE 13

A granular composition was prepared by dissolving the active ingredient in a solvent, spraying the solution obtained on to the granules of pumice and allowing the solvent to evaporate.

| | % wt |
|---|---|
| O,O-diethyl O-2-diethylamino-4-methoxycarbonylmethylpyrimidin-6-yl (Compound No. 5, Table 1) | 5 |
| Pumice granules | 95 |
| | 100% |

EXAMPLE 14

An aqueous dispersion formulation was prepared by mixing and grinding the ingredients recited below in the proportions stated.

| | % wt. |
|---|---|
| O,O-Dimethyl-O-2-diethylamino-4-ethoxycarbonylmethylpyrimidin-6-yl phosphorothionate (Compound No. 6, Table 1) | 40 |
| Calcium lignosulphonate | 10 |
| Water | 50 |
| | 100% |

EXAMPLE 15

Compositions comprising other compounds of Table 1 may be prepared by the methods set out in Examples 11 to 14 above.

EXAMPLE 16

The activity of a number of the compounds was tested against a variety of insect and other invertebrate pests. The compounds were used in the form of a liquid preparation containing 0.1% by weight of the compound except in the tests with Aedes aegypti where the preparation contained 0.01% by weight of the compound. The preparations were made by dissolving each of the compounds in a mixture of solvents consisting of 4 parts by volume of acetone and 1 part by volume of diacetone alcohol. The solutions were then diluted with water containing 0.01% by weight of a wetting agent sold under the trade name LISSAPOL NX until the liquid preparations contained the required concentration of the compound. Lissapol is a Trade Mark.

The test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from 1 to 3 days after the treatment.

The results of the tests are given below in Tables 3 and 4. In these tables the first column indicates the name of the pest species. Each of the subsequent columns indicates the host plant or medium on which it was supported, the number of days which were allowed to elapse after the treatment before assessing the mortality of the pests, and the results obtained for each of the compounds, numbered as in Table 1 above. The assessment is expressed in integers which range from 0 – 3.

0 represents less than 30% kill
1 represents 30–49% kill
2 represents 50–90% kill
3 represents over 90% kill A dash (-) in Tables 3 and 4 indicates that no test was carried out.

TABLE 3

| Pest Species | Support medium | No. of days | Compound No. (Table 1) | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| Tetranychus telarius | | | | | | | | | | | | | | | | |

TABLE 3-continued

| Pest Species | Support medium | No. of days | \multicolumn{14}{c}{Compound No. (Table 1)} |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| (adults) | French bean | 3 | 3 | 3 | 3 | 3 | 3 | 3 | 3 | 3 | 3 | 3 | 3 | 0 | 3 | 3 |
| Tetranychus telarius (eggs) | French bean | 3 | 0 | 0 | 0 | 3 | 0 | 3 | 3 | 1 | 3 | 0 | 2 | 3 | 0 | 0 |
| Aphis fabae | Broad bean | 2 | 3 | 3 | 0 | 3 | 3 | 3 | 3 | 3 | 3 | 3 | 3 | 3 | 3 | 3 |
| Megoura viceae | Broad bean | 2 | 3 | 3 | 0 | 3 | 3 | 3 | 3 | 3 | 3 | 3 | 3 | 3 | 3 | 3 |
| Dysdercus fasciatus | Grain | 2 | — | — | — | — | — | — | 3 | 3 | 0 | 0 | 0 | 3 | 3 | 0 |
| Aedes aegypti (larvae) | Water | 1 | 3 | 3 | 3 | 3 | 3 | 3 | 3 | 3 | 3 | 0 | 3 | 3 | 3 | 3 |
| Aedes aegypti (adults) | Plywood | 1 | 3 | 0 | 0 | 0 | 0 | 0 | 0 | 1 | 0 | 0 | 0 | 0 | 2 | 3 |
| Musca domestica (contact test) | Milk/sugar | 3 | 3 | 3 | 3 | 3 | 3 | 3 | 3 | 3 | 3 | 1 | 3 | 3 | 3 | 3 |
| Musca domestica (residual test) | Plywood | 3 | 2 | 2 | 3 | 3 | 0 | 1 | 0 | 1 | 0 | 0 | 0 | 0 | 0 | 2 |
| Blatella germanica | — | 3 | 2 | 3 | 0 | 23 | 0 | 0 | 3 | 3 | 2 | 0 | 0 | 0 | 0 | 0 |
| Pieris brassicae (larvae) | Cabbage | 2 | 3 | 3 | 3 | 3 | 3 | 3 | 3 | 3 | 3 | 3 | 3 | 3 | 2 | 3 |
| Plutella maculipennis (larvae) | Mustard | 2 | 2 | 2 | 0 | 3 | 0 | 0 | 0 | 1 | 3 | 0 | 0 | 2 | 3 | 0 |
| Phaedon cochleariae | Mustard | 2 | 2 | 3 | 3 | 3 | 3 | 3 | 3 | 3 | 3 | 0 | 3 | 1 | 0 | 3 |
| Calandra granaria | Grain | 2 | 3 | 2 | 1 | 2 | 3 | 3 | 3 | 3 | 3 | 3 | 3 | 3 | 3 | 3 |
| Tribolium confusum | Grain | 2 | 3 | 3 | 0 | 3 | 3 | 0 | 2 | 3 | 3 | 3 | 3 | 3 | 3 | 3 |
| Meloidogyne incognita | Tomato (roots) | 14 | 0 | 3 | 0 | 0 | — | — | 0 | 2 | 2 | 0 | 0 | 0 | 0 | 3 |

TABLE 4

| Pest Species | Support medium | No. of days | \multicolumn{6}{c}{Compound No.(Table 1)} |
|---|---|---|---|---|---|---|---|---|
| | | | 15 | 16 | 17 | 18 | 19 | 20 |
| Tetranychus telarius (adults) | French bean | 3 | 3 | 3 | 3 | 2 | 1 | 3 |
| Aphis fabae | Broad bean | 2 | 3 | 3 | 0 | 0 | 0 | 3 |
| Megoura viceae | Broad bean | 2 | 3 | 3 | 2 | 3 | 0 | 3 |
| Aedes aegypti (larvae) | Water | 1 | 3 | 3 | 3 | 3 | 0 | 3 |
| Musca domestica (contact test) | Milk/water | 3 | 0 | 0 | 3 | 2 | 3 | 2 |
| Pieris brassicae (larvae) | Cabbage | 2 | 3 | 3 | 3 | 3 | 0 | 3 |

Compound Nos. 2 and 6 of Table I were also treated for molluscicidal activity and were found to be toxic to grey field slugs (*Agriolimax reticulatus*).

In the foregoing Tables "contact test" indicates that both the pests and the medium were treated and "residual test" indicates that the medium was treated before infestation with the pests.

We claim:

1. A compound of formula:

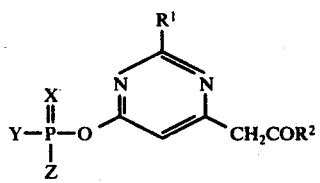

wherein X is oxygen or sulphur; Y is alkoxy containing from one to four carbon atoms, alkylamino containing from one to four carbon atoms, or dialkylamino containing from one to four carbon atoms in each alkyl moiety; Z is alkoxy containing from one to four carbon atoms; $R^1$ is alkyl containing from one to four carbon atoms, phenyl, chlorophenyl, alkylamino containing from one to four carbon atoms, dialkylamino containing from one to four carbon atoms in each alkyl moiety, or N-carboxylic acyl alkylamino containing from one to four carbon atoms in the carboxylic acyl moiety and from one to four carbon atoms in the alkyl moiety; and $R^2$ is alkoxy containing from one to four carbon atoms, amino, alkylamino containing from one to four carbon atoms, dialkylamino containing from one to four carbon atoms in each alkyl moiety, or alkenyl amino containing three to five carbon atoms.

2. A compound according to claim 1 wherein X is oxygen or sulphur; Y and Z are alkoxy containing from one to four carbon atoms; $R^1$ is alkyl containing from one to four carbon atoms or dialkylamino containing from one to four carbon atoms in each alkyl moiety; and $R^2$ is alkoxy containing from one to four carbon atoms.

3. A compound according to claim 1 wherein X is oxygen or sulphur; Y and Z are both methoxy or ethoxy; $R^1$ is diethylamino; and $R^2$ is methoxy or ethoxy.

4. O,O-dimethyl O-2-diethylamino-4-ethoxycarbonylmethylpyrimidin-6-yl phosphorothionate.

* * * * *